(12) United States Patent
Wu

(10) Patent No.: US 10,363,209 B2
(45) Date of Patent: Jul. 30, 2019

(54) COSMETIC COMPOSITION

(71) Applicant: Conopco, Inc., Englewood Cliffs, NJ (US)

(72) Inventor: Chunwei Wu, Temple City, CA (US)

(73) Assignee: Conopco, Inc., Englewood Cliffs, NJ (US)

( * ) Notice: Subject to any disclaimer, the term of this patent is extended or adjusted under 35 U.S.C. 154(b) by 98 days.

(21) Appl. No.: 14/430,941

(22) PCT Filed: Aug. 30, 2013

(86) PCT No.: PCT/EP2013/067971
§ 371 (c)(1),
(2) Date: Mar. 25, 2015

(87) PCT Pub. No.: WO2014/056659
PCT Pub. Date: Apr. 17, 2014

(65) Prior Publication Data
US 2015/0238405 A1    Aug. 27, 2015

(30) Foreign Application Priority Data

Oct. 11, 2012 (WO) ................ PCT/CN2012/082775
Nov. 23, 2012 (EP) .................................... 12194052

(51) Int. Cl.
| A61K 8/60 | (2006.01) |
| A61Q 1/02 | (2006.01) |
| A61Q 19/00 | (2006.01) |
| A61K 8/06 | (2006.01) |
| A61K 8/65 | (2006.01) |
| A61K 8/365 | (2006.01) |
| A61K 8/02 | (2006.01) |
| A61K 8/04 | (2006.01) |
| A61K 8/49 | (2006.01) |
| A61K 8/19 | (2006.01) |

(52) U.S. Cl.
CPC ............ *A61K 8/602* (2013.01); *A61K 8/0241* (2013.01); *A61K 8/042* (2013.01); *A61K 8/06* (2013.01); *A61K 8/19* (2013.01); *A61K 8/365* (2013.01); *A61K 8/494* (2013.01); *A61K 8/65* (2013.01); *A61Q 1/02* (2013.01); *A61Q 19/00* (2013.01); *A61K 2800/26* (2013.01); *A61K 2800/412* (2013.01); *A61K 2800/43* (2013.01); *A61K 2800/592* (2013.01); *A61K 2800/651* (2013.01); *A61K 2800/652* (2013.01); *A61K 2800/654* (2013.01); *A61K 2800/805* (2013.01)

(58) Field of Classification Search
None
See application file for complete search history.

(56) References Cited

U.S. PATENT DOCUMENTS

| 4,844,902 A * | 7/1989 | Grohe ................... A61K 31/57 424/447 |
| 5,972,359 A | 10/1999 | Sine |
| 5,997,890 A | 12/1999 | Sine |
| 6,174,533 B1 | 1/2001 | SaNogueira, Jr. |
| 6,395,691 B1 | 5/2002 | Tsaur |
| 8,663,998 B2 * | 3/2014 | Heacock ................. C09K 9/02 436/166 |
| 2005/0049157 A1* | 3/2005 | MacDonald ......... C11D 3/0042 510/130 |
| 2006/0057084 A1* | 3/2006 | Gonzalez ................ A61K 8/19 424/63 |
| 2006/0058206 A1 | 3/2006 | Walls |
| 2007/0067924 A1 | 3/2007 | Beck |
| 2009/0018047 A1* | 1/2009 | Mundschau ............ A47K 7/03 510/438 |
| 2009/0093063 A1* | 4/2009 | Anslyn .................... A61K 8/11 436/164 |
| 2009/0155321 A1 | 6/2009 | Harichian |
| 2010/0278761 A1 | 11/2010 | Samain et al. |
| 2011/0008399 A1* | 1/2011 | Bugnon ................ C09C 1/0015 424/401 |
| 2011/0021397 A1 | 1/2011 | Horerca |
| 2011/0182826 A1 | 7/2011 | Boyke |
| 2011/0229536 A1* | 9/2011 | Kvitnitsky ........... A61K 8/0212 424/401 |
| 2013/0129652 A1* | 5/2013 | Blin ....................... A61K 8/042 424/63 |
| 2013/0302388 A1* | 11/2013 | Matsuo .................. A61K 8/042 424/401 |

FOREIGN PATENT DOCUMENTS

| CN | 101810545 | 8/2010 |
| CN | 102088946 | 6/2011 |
| DE | 102009031273 | 1/2011 |
| EP | 1172083 | * 1/2002 |
| JP | S63148963 | 6/1988 |
| KR | 20090021584 | 3/2009 |
| WO | WO2009138978 | 11/2009 |
| WO | WO2010056232 | 5/2010 |
| WO | WO2010056233 | 5/2010 |

OTHER PUBLICATIONS

IPRP2 in PCTEP2013067971 dated Sep. 23, 2014. pp. 1 to 11.
Search Report in EP12194052 dated May 16, 2013. pp. 12 to 13.
Search Report in PCTEP2013067971 dated May 9, 2014. pp. 14 to 17.
Written Opinion in EP12194052 dated May 16, 2013. pp. 18 to 20.
Written Opinion in PCTEP2013067971 dated May 9, 2014. pp. 21 to 27.

* cited by examiner

*Primary Examiner* — Robert A Wax
*Assistant Examiner* — Danah Al-Awadi
(74) *Attorney, Agent, or Firm* — Greenberg Traurig, LLP

(57) ABSTRACT

Disclosed is a cosmetic composition comprising particles dispersed in a cosmetically acceptable carrier, wherein the particles comprise redox dye and reducing agent.

13 Claims, No Drawings

COSMETIC COMPOSITION

FIELD OF THE INVENTION

The present invention relates to cosmetic compositions, such as moisturizers. More particularly, the present invention relates to such compositions containing particles wherein the particles comprise a redox dye. The present invention also relates to a process for manufacturing the particles and/or for manufacturing the cosmetics containing them.

BACKGROUND OF THE INVENTION

Even skin color/tone is a major indicia of a healthy looking appearance. Make-up formulas have been designed to mimic a person's skin tones. High loadings of pigments such as titanium dioxide and zinc oxide are optical ingredients necessary for these formulations. These loadings achieve a covering purpose at the expense of inferior tactile sensory properties.

Less pigment-loaded formulas, particularly moisturizers can provide the desired tactile sensory benefits. These formulas, however, do not address facial color issues.

An alternative approach to the matte effect of make-up has been the use of soft focus particles. Here the incoming light is distorted by scattering (lensing). Components of these formulas operate as lenses to bend and twist light into a variety of directions to provide a blurring effect on high-contrast blemishes or spots.

U.S. Pat. No. 5,997,890 (Sine et al.), U.S. Pat. No. 5,972,359 (Sine et al.), and U.S. Pat. No. 6,174,533 B1 (SaNogueira, Jr.) are all directed to topical compositions that provide good coverage of skin imperfections. The solution proposed by these documents is a soft focus effect utilizing a metal oxide with a refractive index of at least about 2 and a neat primary particle size of from about 100 to about 300 nm. Preferred particulates are titanium dioxide, zirconium oxide and zinc oxide.

A significant disadvantage of titanium dioxide, zirconium oxide and zinc oxide is their over-whitening effect upon the skin. An undesirable ashen and patchy appearance is often unfortunately created. Colourants (especially red and/or purple colourants) are able to counter-balance the unnatural whitening effect, but typically even a tiny amount of dye results in heavily-tinted product and we have found that consumers desire moisturizing formulations which do not resemble make-up cosmetics when in-pack.

We have also found that the unwanted ashen/patchy appearance afforded by some pigment systems can be exaggerated on drying. Thus we have recognized a need for compositions which gradually develop more natural skin tone alter application to the skin and concomitant with drying of the product on skin.

US patent application published as US 2009/0155321 A (Conopco, Inc), is directed to a cosmetic composition and method of imparting a healthy appearance to skin which includes using a composition formed with about 0.1 to about 20 percent by weight of the composition of beads, from about 1 to about 80 percent by weight of the beads of a first coloring agent incorporated within a matrix of the beads, and a cosmetically acceptable carrier, the composition having a hue less than 25 degrees, the beads being coated and having an exterior color other than that of the first coloring agent. The beads are said to be relatively unnoticeable within a moisturizer composition but are frangible such that upon being rubbed into the skin, they deliver color effects.

Unfortunately, the present inventors have found that the use of frangible beads as a means of hiding colourants within a formulation has drawbacks. In particular, the beads may not always rupture in a desirable manner and can sometimes leave "streaks" or other uneven regions of color which does not result in an even appearance.

Therefore the present inventors have recognized a need to provide cosmetics which not only deliver a desirable skin appearance but that also impart desirable tactile sensory benefits and/or deliver the in-pack appearance expected of a moisturizer.

TESTS AND DEFINITIONS

Redox Dye

Redox dyes are defined as substances which exist in oxidized and reduced forms having different colours. Preferred are leuco dyes (i.e. dyes in which one form is colourless). A detailed discussion of redox chemistry and redox dyes can be found, for example, in paragraphs [0014] to [0021] of US 2005/0049157 A (McDonald et al) which is hereby incorporated by reference in its entirety.

Reducing Agent

Reducing agents are substances which are capable of keeping a redox dye in a reduced state. A detailed discussion of redox chemistry and reducing agents can be found, for example, in paragraphs [0024] to [0028] of US 2005/0049157 A (McDonald et al) which is hereby incorporated by reference in its entirety.

Particle Size

Where the size of particles is mentioned this means the diameter measurable by scanning electron microscopy (SEM) or transmission electron microscopy (TEM), although SEM is preferred. In the event that a particle is not spherical then "diameter" means the largest distance measurable across the particle.

Leave-On and Wash-off

The term "leave-on" as used with reference to compositions herein means a composition that is applied to or rubbed on the skin, and left thereon.

The term "wash-off" as used with reference to compositions herein means a skin cleanser that is applied to or rubbed on the skin and rinsed off substantially immediately subsequent to application.

Refractive Index

Refractive index values referred to herein are those determined at a temperature of 25° C. and a wavelength of 589 nm unless otherwise stated.

Skin

The term "skin" as used herein includes the skin on the face (except eye lids and lips), neck, chest, abdomen, back, arms, hands, and legs. Preferably "skin" means skin on the face.

Miscellaneous

Except in the examples, or where otherwise explicitly indicated, all numbers in this description indicating amounts of material or conditions of reaction, physical properties of materials and/or use may optionally be understood as modified by the word "about".

All amounts are by weight of the final composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

SUMMARY OF THE INVENTION

In a first aspect, the present invention is directed to a cosmetic composition comprising particles dispersed in a cosmetically acceptable carrier, wherein the particles comprise redox dye and reducing agent.

In a second aspect, the present invention provides a process comprising the steps of:
 a) providing a mixture of redox dye, reducing agent, polymer and solvent;
 b) drying the mixture; and
 c) forming the mixture into particles.

All other aspects of the present invention will more readily become apparent upon considering the detailed description and examples which follow.

DETAILED DESCRIPTION

The present inventors have found that providing dispersed particles comprising redox dye and reducing agent allows for formulation of cosmetic compositions, like moisturizers which have the in-pack appearance expected by consumers but which deliver a desirable skin appearance on and/or after application to the skin.

There is no limitation to the redox dye that may be used in the present invention, save that the dye is compatible with cosmetic ingredients and safe for topical application to skin. Most preferred are dyes which are red or purple in the oxidized state as these give more natural skin appearance. More preferable are dyes which are red or prurple in the oxidized state but colourless in the reduced state as such dyes allow not only for natural skin appearance but also allow for formulation of in-pack cosmetics that are not coloured by the dye. Examples of such dyes include, for example, Vat red 1 (6,6-dichloro-4,4-dimethyl-[2,2-bibenzo[b]thiophene]-3,3-dione, C.I. 73360), solubilised Vat red 1 (disodium 6,6'-dichloro-4,4'-dimethyl[2,2'-bibenzo[b]thiophene]-3,3'-diyl disulphate, C.I. 73361), carmine (7-α-D-Glucopyranosyl-9,10-dihydro-3,5,6,8-tetrahydroxy-1-methyl-9,10-dioxoanthracenecarboxylic acid, C.I. 75470, also known as Natural red 4), Safranin (3,7-diamino-2,8-dimethyl-5-phenylphenazinium chloride, C.I. 50240, also known as Basic red 2), Neutral red (3-Amino-7-dimethyl-amino-2-methylphenazine hydrochloride, C.I. 50040, also known as Basic red 5), solubilised alizarin red (3,4-Dihydroxy-9,10-dioxo-2-anthracenesulfonic acid sodium salt, C.I. 58005) or a mixture thereof. Even more preferred is solubilised Vat red 1, carmine, solubilised alizarin red and mixtures thereof.

The amount of dye employed in the composition will depend, to some extent on the extinction coefficient of the dye and the degree of skin colouring desired. Typically, however the cosmetic composition comprises the dye in an amount of from 0.0001 to 5% by total weight of the cosmetic composition, more preferably from 0.001 to 2%, more preferably still 0.01 to 1% and most preferably 0.05 to 0.5%.

Preferably the particles comprise a large amount of the dye such that only a small amount of particles are required to deliver the desired amount of colour, thus limiting the effect of the particles on properties of the cosmetic composition such as tactile sensory. Thus the particles preferably comprise the dye in an amount of at least 1% by weight of the particles, more preferably at least 2%, more preferably still at least 5% and most preferably from 7 to 50%.

The reducing agent employed in the present invention is limited only to the extent that it is suitable for keeping the redox dye in a reduced state in-pack. Examples of suitable reducing agents include, for example:
 alpha hydoxy acid (AHA), including but not limited to glycolic acid, lactic acid, citric acid, mandelic acid, tartaric acid and mixtures thereof;
 reducing sugar, including but not limited to glucose, galactose, xylose and mixtures thereof;
 hydroquinone;
 ascorbate;
 cysteine;
 $NaS_2O_3$;
 $NaNO_2$;
 $NaBH_4$; or
 a mixture thereof.

Even more preferred is ascorbate, reducing sugar, AHA or a mixture thereof.

The amount of reducing agent employed in the composition will depend, to some extent on the reduction potential of the agent and the dye as well as the amount of dye. Typically, however the cosmetic composition comprises the reducing agent in an amount of from 0.001 to 10% by total weight of the cosmetic composition, more preferably from 0.01 to 5%, more preferably still 0.1 to 2% and most preferably 0.2 to 1%.

The particles preferably comprise the reducing agent in an amount of at least 1% by weight of the particles, more preferably at least 5%, more preferably still at least 7% and most preferably from 10 to 50%.

To enhance the mechanical robustness of the particles and/or to help with camouflaging any residual colour of the dye in-pack it is preferred that the particles comprise a further material which forms a carrier matrix for the dye and reducing agent. Most preferred as the matrix material is polymer as polymers have good mechanical properties and/or are convenient to shape into particulate form. Thus in a preferred embodiment the particles comprise polymer.

The preferred polymers are biopolymers such as polysaccharides, oligosaccharides and/or proteins owing to their good compatibility with water and cosmetic ingredients. Even more preferred are gel-forming biopolymers as these materials can form hydrogels which are swellable in water but do not dissolve and so retain the dye and reducing agent substantially within the particles. Therefore most preferably the polymer is selected from gelatin, starches (including hydrolysed starches such as maltodextrins), pectin. chitosan, carrageenan, galactomannan polymers (such as locust bean gum), gum arabic, cellulose polymers, alginate, agar, polylysine or mixtures thereof.

Preferably the majority of the particle is formed from polymer. Thus it is preferred that the particles comprise polymer in an amount of at least 50% by weight of the particles, more preferably at least 60%, even more preferably at least 70% and most preferably from 80 to 98%.

The amount of particles employed in the cosmetic composition will depend, to some extent on the content of dye in the particles and the degree of colour required on application of the cosmetic to skin. Typically, however, the cosmetic composition comprises the particles in an amount of at least 0.01% by weight of the composition, more preferably at least 0.1%, more preferably still at least 0.5%, even more preferably at least 1% and most preferably at least 2%. It is preferred, however that the amount of particles is not too high, otherwise their presence may bring unwanted sensory properties. Therefore it is preferred that the cosmetic composition comprises the particles in an amount no greater than 20% by weight of the composition, more preferably no greater than 15%, more preferably still no greater than 10% and most preferably less than 7%.

To aid ease of dispersion of the particles in the cosmetic composition and avoid unwanted sedimentation it is preferred that the particles are micronized. More preferably from 50 to 100% by weight of the particles have a particle size of from 0.1 to 100 µm, more preferably still from 0.5 to 50 µm, most preferably from 1 to 20 µm.

The particles may be made by any suitable process including for example, emulsion polymerization chemical cross-linking, physical cross-linking or a combination thereof. However the present inventors have surprisingly found that particles manufactured by spray drying have excellent robustness and do not leave "streaks" or other unwanted marks on application. Most preferably the particles are formed by a process comprising spray drying a mixture comprising redox dye, reducing agent, polymer and solvent (such as, for example, water).

In a preferred aspect of the invention, the particles are manufactured by a process comprising the steps of:
 a) providing a mixture of the redox dye, reducing agent, polymer and a solvent;
 b) drying the mixture; and
 c) forming the mixture into particles.

The particles are preferably formed by spray drying the mixture, in which case steps (b) and (c) occur simultaneously.

The solvent is preferably an aqueous solvent, more preferably the solvent comprises at least 60% water by weight of the solvent, more preferably at least 80% and most preferably from 90 to 100%.

Preferably the mixture in step (a) comprises at least 70% solvent by weight of the mixture, more preferably at least 80%, more preferably still at least 90% and most preferably from 95 to 99.9%.

Preferably the mixture is dried in step (b) such that the solvent content in the particles is less than 20% by weight of the particles, more preferably less than 15%, more preferably still less than 10% and most preferably from 0.01 to 8%.

The cosmetic composition of this invention is a composition suitable for topical application to human skin, including leave-on and wash-off products. Preferably the term encompasses a fluid liquid, and particularly a moisturizer rather than a make-up product. Most preferred are leave-on compositions.

In certain embodiments the cosmetic composition comprises particles which impart opacity to skin, hereafter term "optical particles". The optical particles are typically particles of high refractive index materials. For example the optical particles may have a refractive index of greater than 1.3, more preferably greater than 1.7 and most preferably from 2.0 to 2.7. Examples of such optical particles are those comprising bismuth oxy-chloride, boron nitride, barium sulfate, mica, silica, titanium dioxide, zirconium oxide, iron oxide, aluminium oxide, zinc oxide or combinations thereof.

Most preferred are particles comprising zinc oxide, zirconium oxide, titanium dioxide or a combination thereof as these materials have especially high refractive index. Preferably the composition comprises optical particles in an amount of from 0.001 to 10 wt %, more preferably 0.01 to 7 wt %, more preferably still 0.05 to 5 wt % and most preferably 0.1 to 2 wt %.

Compositions comprising optical particles often have a problem in that as the composition dries on the skin it becomes whiter and gives the skin an even more "ashen" appearance. For such compositions the present invention has particular advantages in that the redox dye increasingly oxidizes as the composition dries and the resulting development of colour may somewhat counteract the whitening effect of the optical particles whilst retaining the ability of composition to opacify and mask skin blemishes.

Compositions of the present invention will also include a cosmetically acceptable carrier. Water is the most preferred carrier. Amounts of water may, for example, range from 1 to 99%, preferably from 5 to 90%, more preferably from 35 to 70%, optimally between 40 and 60% by weight of the cosmetic composition. Ordinarily the compositions will be water and oil emulsions, which in some embodiments may be oil-in-water emulsions. Preferred emulsions are the water-in-oil variety.

Where the carrier is an emulsion, it is preferred that the particles are dispersed in the oil phase of the water and oil emulsion as this may improve the stability of the dye in the composition.

Emollient materials may be included as carriers in compositions of this invention. These may be in the form of silicone oils, synthetic esters and/or hydrocarbons. Amounts of the emollients may range, for example, anywhere from 0.1 to 95%, more preferably between 1 and 50% by weight of the composition.

Silicone oils may be divided into the volatile and nonvolatile variety. The term "volatile" as used herein refers to those materials which have a measurable vapor pressure at ambient temperature (25° C.). Volatile silicone oils are preferably chosen from cyclic (cyclomethicone) or linear polydimethylsiloxanes containing from 3 to 9, preferably from 4 to 5, silicon atoms. In many liquid versions of compositions according to the present invention, the volatile silicone oils may form a relatively large component of the compositions as carriers. Amounts may range, for example, from 5% to 80%, more preferably from 20% to 70% by weight of the composition.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5 \times 10^{-6}$ to 0.1 m$^2$/s at 25° C. Among the preferred nonvolatile emollients useful in the present compositions are the polydimethyl siloxanes having viscosities from about $1 \times 10^{-5}$ to about $4 \times 10^{-4}$ m$^2$/s at 25° C.

Organopolysiloxane crosspolymers can be usefully employed. Representative of these materials are dimethicone/vinyl dimethicone crosspolymers and dimethicone crosspolymers available from a variety of suppliers including Dow Corning (9040, 9041, 9045, 9506 and 9509), General Electric (SFE 839), Shin Etsu (KSG-15, 16 and 18 [dimethicone/phenyl vinyl dimethicone crosspolymer]), and Grant Industries (Gransil brand of materials), and lauryl dimethicone/vinyl dimethicone crosspolymers supplied by Shin Etsu (e.g. KSG-31, KSG-32, KSG-41, KSG-42, KSG-43 and KSG-44). Amounts of the aforementioned silicone elastomers (when present) will usually be from 0.1 to 20% by weight dissolved usually in a volatile silicone oil such as cyclomethicone.

When silicones are present in large amounts as carrier and water is also present, the systems may be oil continuous. These normally will require emulsification with a water-in-oil emulsifier such as a dimethicone copolyol (e.g. Abil EM-90 which is cetyl dimethicone copolyol).

Among the ester emollients are:
a) Alkenyl or alkyl esters of fatty acids having 10 to 20 carbon atoms. Examples thereof include isoarachidyl neopentanoate, isodecyl neopentanoate, isononyl isononanoate, cetyl ricinoleate, oleyl myristate, oleyl stearate, and oleyl oleate.
b) Ether-esters such as fatty acid esters of ethoxylated fatty alcohols.
c) Polyhydric alcohol esters. Butylene glycol, ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols. Exemplative is pentaerythrityl tetraethylhexanoate.
d) Wax esters such as beeswax, spermaceti wax and tribehenin wax.
e) Sterols esters, of which cholesterol fatty acid esters are examples thereof.
f) Sugar ester of fatty acids such as sucrose polybehenate and sucrose polycottonseedate.

Of particular use also are the $C_{12-15}$ alkyl benzoate esters sold under the Finsolve brand.

Hydrocarbons which are suitable cosmetically acceptable carriers include petrolatum, mineral oil, $C_{11}$-$C_{13}$ isoparaffins, polyalphaolefins, and especially isohexadecane, available commercially as Permethyl 101A from Presperse Inc.

Humectants of the polyhydric alcohol-type can be employed as cosmetically acceptable carriers. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. The amount of humectant may range, for example, anywhere from 0.5 to 50%, more preferably between 1 and 15% by weight of the composition. Most preferred is glycerol (also known as glycerin). Amounts of glycerin may range, for example, from 1% to 50%, more preferably from 10 to 35%, optimally from 15 to 30% by weight of the composition.

Besides cosmetically acceptable carriers, the compositions of this invention may include a variety of other functional ingredients. Sunscreen actives may be included in compositions of the present invention. These will be organic compounds having at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-d imethoxybenzophenone, Octabenzone; 4-Isopropyldibenzoylmethane; Butylmethoxydibenzoylmethane; Etocrylene; and 4-isopropyl-dibenzoylmethane). Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Particularly preferred are such materials as ethylhexyl p-methoxycinnamate, available as Parsol MCX®, Avobenzone, available as Parsol 1789®, Dermablock OS® (octylsalicylate) and Mexoryl SX® (with INCI name of Terephthalylidene Dicamphor Sulfonic Acid). Amounts of the organic sunscreen agent may range, for example, from 0.1 to 15%, more preferably from 0.5% to 10%, optimally from 1% to 8% by weight of the composition.

A variety of thickening agents may be included in the compositions. Illustrative but not limiting are stearic acid, Acrylamide/Sodium Acryloyldimethyltaurate Copolymer (Aristoflex AVC), Hydroxyethyl Acrylate/Sodium Acryloyldimethyltaurate Copolymer, Aluminum Starch Octenyl Succinate, Polyacrylates (such as Carbomers including Carbopol® 980, Carbopol® 1342, Pemulen TR-2® and the Ultrez® thickeners), Polysaccharides (including xanthan gum, guar gum, pectin, carageenan and sclerotium gums), celluloses (including carboxymethyl cellulose, ethyl cellulose, hydroxyethyl cellulose and methyl hydroxymethyl cellulose), minerals (including talc, silica, alumina, mica and clays, the latter being represented by bentonites, hectorites and attapulgites), magnesium aluminum silicate and mixtures thereof. Amounts of the thickeners may range, for example, from 0.05 to 10%, more preferably from 0.3 to 2% by weight of the composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, butyl paraben, isobutyl paraben, imidazolidinyl urea, sodium dehydroacetate and benzyl alcohol. The preservatives should be selected having regard for the use of the composition and possible incompatibilities between the preservatives and other ingredients in the composition. Preservatives are preferably employed in amounts ranging from 0.01% to 2% by weight of the composition.

Compositions of the present invention may also contain vitamins and flavonoids. Illustrative water-soluble vitamins are Niacinamide, Vitamin $B_2$, Vitamin $B_6$, Vitamin C and Biotin. Among the useful water-insoluble vitamins are Vitamin A (retinol), Vitamin A Palmitate, ascorbyl tetraisopalmitate, Vitamin E (tocopherol), Vitamin E Acetate and DL-panthenol. A particularly suitable Vitamin $B_6$ derivative is Pyridoxine Palmitate. Among the preferred flavonoids are glucosyl hesperidin and rutin. Total amount of vitamins or flavonoids when present in compositions according to the present invention may range, for example, from 0.001 to 10%, more preferably from 0.01% to 1%, optimally from 0.1 to 0.5% by weight of the composition.

Desquamation agents are further optional components. Illustrative are the alpha-hydroxycarboxylic acids and beta-hydroxycarboxylic acids and salts of these acids. Among the former are salts of glycolic acid, lactic acid and malic acid. Salicylic acid is representative of the beta-hydroxycarboxylic acids. Amounts of these materials when present may range from 0.1 to 15% by weight of the composition.

A variety of herbal extracts may optionally be included in compositions of this invention. Illustrative are pomegranate, white birch (Betula Alba), green tea, chamomile, licorice, boswellia serrata, olive (Olea Europaea) leaf, arnica montana flower, lavandula angustifolia, and extract combinations thereof. The extracts may either be water soluble or water-insoluble carried in a solvent which respectively is hydrophilic or hydrophobic. Water and ethanol are the preferred extract solvents.

Miscellaneous other adjunct cosmetic ingredients that may be suitable for the present compositions include ceramides (e.g. Ceramide 3 and Ceramide 6), conjugated linoleic acids, colorants (e.g. iron oxides), metal (manganese, copper and/or zinc) gluconates, allantoin, palmitoyl pentapeptide-3, amino acids (e.g. alanine, arginine, glycine, lysine, proline, serine, threonine, glumatic acid and mixtures thereof), trimethylglycine, sodium PCA, chelator like disodium EDTA, opacifiers like titanium dioxide, magnesium aspartate, and combinations thereof. Amounts may, for example, vary from 0.000001 to 3% by weight of the composition.

A small amount of emulsifying surfactant may be present. Surfactants may be anionic, nonionic, cationic, amphoteric and mixtures thereof. Levels may range, for example, from 0.1 to 5%, more preferably from 0.1 to 2%, optimally from 0.1 to 1% by weight. Advantageously the amount of surfactant present should not be sufficient for lather formation. In these instances, less than 2% by weight, preferably less than 1%, and optimally less than 0.5% by weight surfactant is present. Emulsifiers like PEG-100 stearate may be used as well as emulsion stabilizers like cetearyl alcohol and ceteareth-20 may be used and typically in amounts that do not exceed 5 percent by weight of the composition.

Other optional additives suitable for use in the composition of this invention include cationic ammonium compounds to enhance moisturization. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from 0.01 to 30%, and more preferably from about 0.1 to about 15% by weight of the composition.

When cationic ammonium compounds are used, optional additives for use with the same are moisturizing agents such as substituted ureas like hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-di-hydroxyethyl urea; N,N'-di-hydroxypropyl urea; N,N,N'-tri-hydroxyethyl urea; tetra (hydroxymethyl) urea; tetra(hydroxyethyl) urea; tetra (hydroxypropyl) urea; N-methyl-N'-hydroxyethyl urea; N-ethyl-N'-hydroxyethyl urea; N-hydroxypropyl-N'-hydroxyethyl urea and N,N'dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance. Such substituted ureas, while desirable in moisturizing formulations, are only selected for use when compatible with sunless tanning agent or agents (if presemt) used in the compositions of this invention.

Amounts of substituted urea, when used, in the composition of this invention range from 0.01 to 20%, more preferably from 0.5 to 15%, and most preferably from 2 to 10% based on total weight of the composition and including all ranges subsumed therein.

When cationic ammonium compound and substituted urea are used, in a most especially preferred embodiment at least from 0.01 to 25%, more preferably from 0.2 to 20%, and most preferably from 1 to 15% humectant, like glycerine, is used, based on total weight of the composition and including all ranges subsumed therein.

When making the compositions of this invention, ingredients are typically mixed with moderate shear under atmospheric conditions. Preferably, the compositions display a pH from 4 to 6.

Packaging for the composition of this invention can be a jar or tube as well as any other format typically seen for cosmetic, cream, washing and lotion type products. The compositions may be applied topically and preferably 1-4 milligrams of composition is applied per square centimeter of skin. The composition is preferably substantially white or colourless (transparent) when in packaged form but is transformable to a coloured composition on application to skin The following examples are provided to facilitate an understanding of the invention. The examples are not intended to limit the scope of the claims.

EXAMPLES

Example 1

This example demonstrates manufacture of particles suitable for use in the present invention.

An aqueous precursor solution was prepared containing 0.2 wt % safranin, 0.4 wt % $NaBH_4$ and 2.5 wt % gelatin in deionised water. The solution was prepared by first dissolving the gelatin in hot (~70° C.) water, cooling to around 40° C. and then adding the dye and reducing agent.

The aqueous precursor solution was then fed to a spray dryer (SY-6000 manufactured by Bilon) at a rate of around 15 ml/min and dried in a 250° C. air flow.

The obtained powder was visualized by SEM and the micrographs showed spheroidal particles with sizes ranging from 1 to 10 μm.

Example 2

This example demonstrates manufacture of particles suitable for use in the present invention.

An aqueous precursor solution was prepared containing 0.25 wt % carmine, 2.5 wt % lactic acid and 10.0 wt % gelatine in deionised water. The solution was prepared by first dissolving the gelatine in hot water, cooling down to about 40° C. and then adding the dye and reducing agent.

The precursor solution was then spray dried in a similar manner as described in Example 1.

Example 3

This example demonstrates colour change of an aqueous composition comprising particles of the invention.

A 5 wt % dispersion of the particles of Example 1 was prepared. The dispersion was clear and colourless.

A drop of the dispersion was spread on white card and allowed to dry at room temperature (25° C.). After around 5 minutes the area of card treated with the dispersion began to show a visible pink colour which further developed as the composition dried until after 30 minutes a strong pink coloured area was apparent.

Example 4

This example demonstrates colour change of an oil-based composition comprising particles of the invention.

A dispersion of the particles of Example 1 was prepared with a final composition of 2 wt % of the particles and 4 wt % micronized titanium dioxide in DC 245 silicone oil. The dispersion was white.

A drop of the dispersion was spread on white card and allowed to dry at room temperature (25° C.) until a strong pink coloured area was apparent.

Example 5

This example demonstrates colour change of an oil-in-water cosmetic comprising particles of the invention.

A commercial moisturizing cream (Pond's™ Flawless White Night Cream) was used as the carrier with the particles of Example 1 incorporated in the aqueous phase in an amount of 2 wt % (based on the total composition).

Slightly pinkish coloured creams were achieved and retained in-bottle regardless of the presence of the particles of Example 1.

When the cream containing the particles of Example 1 was applied to white card, starting from a very pale hue at the beginning, a growing pink colour was progressively developed.

Example 6

This example demonstrates colour change of a water-in-oil cosmetic comprising particles of the invention.

A commercial moisturizing cream (Pond's™ Age Miracle) was used as the carrier with the particles of Example 1 incorporated in the oil phase in an amount of 2 wt % (based on the total composition).

Slightly pinkish coloured creams were achieved and retained in-bottle regardless of the presence of the particles of Example 1.

When the cream containing the particles of Example 1 was applied to white card, starting from a very pale hue at the beginning, a growing pink colour was progressively developed.

The invention claimed is:

1. A cosmetic composition comprising particles dispersed in a cosmetically acceptable carrier,
    wherein the particles comprise polymer, redox dye and reducing agent;
    wherein the cosmetically acceptable carrier is a water and oil emulsion;
    wherein the particles are dispersed in the oil phase of the water and oil emulsion;
    wherein from 50 to 100% by weight of the particles have a particle size of from 1 to 20 μm;
    wherein the particles comprise polymer in an amount of at least about 80 to 98% by weight of the particles; and
    wherein the cosmetic composition comprises the particles in an amount of at least 2% and less than 7%.

2. The composition as claimed in claim 1, wherein the redox dye is selected from Vat red 1, solubilised Vat red 1, carmine, Safranin, Neutral red, solubilised alizarin red or a mixture thereof.

3. The composition as claimed in claim 1, wherein the reducing agent is selected from reducing sugar, ascorbate, alpha hydroxyl acid, hydroquinone, cysteine, NaS2O3, NaNO2, NaBH4 or a mixture thereof.

4. The composition as claimed in claim 1, wherein the polymer is a biopolymer.

5. The composition as claimed in claim 4, wherein the particles comprise a hydrogel.

6. The composition as claimed in claim 1, wherein the cosmetic composition is a moisturizer.

7. A process for forming the particles of claim 1 comprising the steps of: a) providing a mixture of redox dye, reducing agent, polymer and solvent; b) drying the mixture; and c) forming the mixture into particles.

8. The process as claimed in claim 7, wherein the particles are formed by spray drying the mixture.

9. The process as claimed in claim 7, wherein the particles are combined with a cosmetically acceptable carrier.

10. The process as claimed in claim 9, wherein the cosmetically acceptable carrier is a water and oil emulsion.

11. The process as claimed in claim 10, wherein the particles are added to the oil phase of the water and oil emulsion.

12. The composition as claimed in claim 4, wherein the biopolymer is selected from the group consisting of polysaccharide, oligosaccharide protein and a mixture thereof.

13. The composition as claimed in claim 1, wherein the water and oil emulsion is a water-in-oil emulsion.

* * * * *